United States Patent [19]
de la Guardia

[11] B 3,981,681
[45] Sept. 21, 1976

[54] DEPILATORY FORMULATION
[75] Inventor: Mario de la Guardia, Savannah, Ga.
[73] Assignee: Carson Products Company, Savannah, Ga.
[22] Filed: Apr. 16, 1974
[21] Appl. No.: 461,352
[44] Published under the second Trial Voluntary Protest Program on January 13, 1976 as document No. B 461,352.

[52] U.S. Cl. .................................................. 8/161
[51] Int. Cl.² ........................................ A61K 7/155
[58] Field of Search ...................................... 8/161

[56] References Cited
UNITED STATES PATENTS
3,271,258   9/1966   Zviak et al. ........................... 8/94.16
3,384,548   5/1968   Zviak et al. ............................. 8/160

FOREIGN PATENTS OR APPLICATIONS
1,956,002   5/1970   Germany

OTHER PUBLICATIONS
Chemical Abstracts, vol. 72: 124997m, (1970).

Primary Examiner—Donald B. Moyer
Attorney, Agent, or Firm—Murray and Whisenhunt

[57] ABSTRACT

A stable, aqeuous depilatory composition is disclosed, wherein the composition contains, as the essential active ingredients, alkali metal silicates, alkali earth metal salts of α-and/or β-mercapto carboxylic acids and thiourea.

The composition is useful in removing facial hair (beard) with the hair being removed in a short period of time, for instance 4 – 7 minutes or so, depending on toughness of the beard and with minimal incidence of skin irritation in the average user.

13 Claims, No Drawings

DEPILATORY FORMULATION

BACKGROUND OF THE INVENTION

Depilatories have been used for quite a period of time to remove body hair. Depilatory for such use usually requires application times of at least 15 minutes, and often up to 20 or 30 minutes, for adequate depilation. Along with adequte hair removal, the composition must exhibit little if any skin irritation.

Depilatory compositions are generally available in the form of powders, creams, and aerosol foams.

A use for depilatories also exists in the removal of facial hair, especially for Negro males. The facial hairs of such individuals tend to ingrow quite easily with the result of a benign non-contagious dermatitis of the beard area clinically known as Pseudo-Folliculitis Barbe. This is caused by the removal of facial hair with the aid of a razor which generally leaves relatively sharp points on the ends of the hair, with the resulting pointed hair readily penetrating the face, if the hair has sufficient curl to cause the point to contact the skin prior to the next cycle of hair removal, such as shaving. Thus, a substantial need exists among Negro males for a facial hair depilatory. Several facial hair (beard) depilatory products have been previously marketed, but most of these products have been marketed in the form of dry powders, which must be mixed with water just prior to application to the face. No fast cutting facial hair (beard) depilatory creams have been marketed to date, because of the instability of some of the advantageous depilatory components in cream form, and/or irritability.

When the facial hair of Negro males is removed by a chemical agent or depilatory, the hair end is generally soft and fluffy, and generally will not penetrate the skin if allowed to contact the skin surface. Thus, a significantly reduced incidence of ingrown facial hairs can be observed by using chemical depilatory agents. Normally, however, because of the fact that the depilatories must be strong enough to remove facial hair within a short period of time, e.g. 4 – 7 minutes or so, the depilatories exhibit some irritation to the skin. Because of this skin irritation, it is generally recommended that chemical depilatories be used not more often than every other day, with no hair removal on the alternate days.

The use of alkali metal and alkali earth metal salts of α- and β-mercapto carboxylic acids as depilatory agents is known to the art, note, e.g., U.S. Pat. No. 2,823,168 and 3,154,470.

DESCRIPTION OF THE INVENTION

The depilatory composition of the present invention exhibits reduced hair cutting times or depilation times, together with minimal skin irritation. The face can be treated with the depilatory of the present invention, and substantially complete hair removal can be achieved within 4 – 7 minutes. Even with this short depilation time, the average Negro male will exhibit no skin irritation when using the composition of the present invention not more often than every other day.

The increased rate of hair removal obtained by the present invention is believed to be due to a synergistic effect between the two accelerators contained therein. The α- or β-mercapto carboxylic acid salts, such as an alkaline earth metal thioglycolate, is the primary depilating agent, and the silicate and the thiourea function as accelerators for this depilating agent. The fact that a synergistic effect is obtained is indicated by the fact that removal by the composition of the present invention takes significantly less time than obtained by similar compositions containing an equivalent amount of only the silicate or only the thiourea.

The composition of the present invention is based upon four essential ingredients. These ingredients are water, alkali metal silicates, alkaline earth metal α- and/or β-mercapto carboxylic acid salts, and thiourea. The composition generally contains, based on one part of the silicate, about 5 – 200 parts of the mercapto carboxylic acid salt and about 1 – 50 parts of thiourea, and enough water to form a stable smooth cream, generally about 25 to 90%, and preferably about 64 to 70% of water. Generally the mercapto carboxylic acid salt will be used in amounts of less than 100 parts, preferably about 6 – 50 parts, and more preferably about 10 – 20 parts, based on one part of the silicate. The thiourea, on the other hand, is preferably used in an amount of 3 – 35 parts, more preferably about 5 – 15 parts, per part of silicate.

The alkali metal silicate is preferably sodium metasilicate, although potassium and lithium metasilicates, for instance, can be used as partial or full replacements therefor. The silicate may be in the ortho form, which is normally converted to the metasilicate at the high pH's used in the depilatory composition. The silicate may be of various degrees of hydration, with sodium metasilicate pentahydrate being found to be particularly effective. Mixtures of silicates can be used.

The α- or β-mercapto carboxylic acid salt generally contains 2 to 5 carbon atoms, preferably 3 carbon atoms, and is preferably calcium thioglycolate. Other suitable mercapto carboxylic acid salts include barium thioglycolate, strontium thioglycolate, maganesium thioglycolate, and calcium, barium, strontium or magnesium thiolactates, and mixtures may be used.

The mercapto carboxylic acid salt may be generally represented by the structural formula:

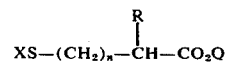

wherein $n$ is 0 or 1, R is hydrogen or lower alkyl of 1 or 2 carbon atoms, Q is an alkaline earth metal and X is hydrogen or, when Q is divalent, a bond linking Q to the sulfur atom.

The pH of the depilatory composition should be adjusted to a value of about 11.5 - about 12.7, although the preferred pH range is 12 - 12.5. Normally, products having a pH of 11.5 will be slow acting, and products having a pH of 12.7 will irritate the skin when used. Generally, alkalizing agents will be used to adjust the pH, with calcium hydroxide, for instance, being a suitable alkalizing agent due to the reduced irritation encountered therewith. Other alkalizing agents which could be used include sodium hydroxide, lithium hydroxide, strontium hydroxide, and the like, but it should be understood that substantially greater irritation may be encountered with such products and for that reason they are generally avoided.

In commercial depilatory creams based on the present invention, a number of other ingredients will generally be present. These ingredients, while not essential, generally add to the overall properties of the composition. For instance, a suitable filler, such as calcium carbonate, whitening, clays, talc, and the like, will be normally present. Emulsifiers and surfactants will generally be present. Suitable ingredients include emulsifiers such as waxes sold under the name "Cetomacrogol", such as the product sold under the trade name "Cyclochem NI", sold by Cyclo Chemicals, and "Evanol", sold by Evans Chemetics, and the surfactant such as sodium lauryl sulfate. It is generally preferred to utilize chelating agents to complex iron and polyvalent metals to prevent discoloration. A chelating agent sold by Ciba-Geigy under the trade name "Chel 242PN" has been found to be quite effective. A thickener will normally be utilized, such as, for instance, the product "Cab-O-Sil", a pyrogenic silica sold by Cabot Corp. Finally, a fragrance will generally be added to mask any unpleasant odors.

A typical formulation containing the optional ingredients might contain the following:

| Component | Weight Percent |
| --- | --- |
| Filler | 5 – 7% |
| Emulsifying Wax | 2.5 – 5.0% |
| Surfactant | 0.02% |
| Chelating agent | 0.45% |
| Thickener | 0.1 – 1.0% |
| Alkalizing agent | 5.0% |
| Fragrance | 0.6% |
| Alkali Metal Silicate | 0.1 – 1.0% |
| α- and/or β-Mercapto Carboxylic Acid Salt | 5 – 10% |
| Thiourea | 3 – 7% |
| Water | 63 – 78% |

The maximum solubility of calcium thioglycolate is about 6 weight percent. If the calcium thioglycolate is increased to 10 weight percent, the resulting product will generally cut hair faster. The sodium metasilicate or other silicate is an accelerator which speeds the hair cutting. Thiourea is also an accelerator, and the combination of thiourea and silicate accelerators greatly increases the hair cutting rate of the composition.

The silicate is the primary skin irritant in the composition of the present invention, with the mercapto carboxylic acid salt being a secondary skin irritant. The thiourea results in little or no skin irritation. Thus, when formulating for skins of particular sensitivities, these factors should be kept in mind. However, the preferred compositions described above will generally result in little or no irritation for the user. These compositions generally result in substantially complete hair removal within 4 – 7 minutes.

A major advantage of the depilatory composition described hereinabove, in addition to the fast depilation rate and minimal skin irritation encountered therewith, is extended shelf stability. The compositions of the present invention can generally be stored under ambient conditions for at least 3 months. The preferred composition has been subjected to accelerated shelf life tests. Test results indicate that the product is stable after 30 days in an oven at 110°F and after two freeze thaw cycles. This should be equivalent to a shelf life of a year or more at ambient conditions.

EXAMPLES OF THE INVENTION

EXAMPLE 1

A depilatory composition was made based on the following formula:

| Ingredients | Weight Percent |
| --- | --- |
| Filler (calcium carbonate) | 6.0% |
| Emulsifying wax (Cetomacrogol) | 3.5% |
| Emulsifier (sodium lauryl sulfate) | 0.02% |
| Chelating agent (Chel 242PN) | 0.45% |
| Thickening agent (CAB-O-SIL) | 0.5% |
| Water | 70.43% |
| Sodium metasilicate pentahydrate | 0.5% |
| Calcium thioglycolate trihydrate | 8.0% |
| Alkalizing agent (calcium hydroxide) | 0.5% |
| Thiourea | 5.0% |
| Fragrance | 0.6% |

The pH of the above formula was 12.3, and the composition was in the form of a smooth cream. The shelf life was calculated to be more than a year based on our accelerated aging studies.

The composition was applied to the faces of unshaven Negro males and allowed to remain in contact with their faces for about 6 minutes. The composition was then washed from the faces, and substantially complete depilation was observed. No visible skin irritation could be noted, and the users reported no burning sensation or other adverse indicia of irritation.

The silicate used in the above formulation could be replaced by the other alkali metal silicates described hereinabove, and the calcium thioglycolate could be replaced by the other alkaline earth metal α-or β-mercapto carboxylic acid salts described hereinabove, with similar results.

What is claimed is:
1. A stable aqueous depilatory composition having a pH of about 11.5 to about 12.7 comprising, as the essential active ingredients,
   a. one part of at least one alkali metal silicate, wherein the amount of said alkali metal silicate is about 0.1 to 1.0 weight percent, based on the total weight of said composition,
   b. 5 to 200 parts of at least one alkaline earth metal acid salt, wherein the acid is selected from the group consisting of thioglycolic acid and thiolactic acid, and
   c. 1 to 50 parts of thiourea, wherein the composition has a shelf stability under ambient conditions of at least three months.
2. Composition according to claim 1, wherein the composition has a pH of 12 – 12.5.
3. Composition according to claim 2, wherein the alkaline earth metal α-or β-mercapto carboxylic acid salt is calcium thioglycolate.
4. Composition according to claim 2, wherein said silicate is sodium silicate.
5. Composition according to claim 2, wherein said composition contains one part of sodium metasilicate, from 6 – 50 parts of calcium thioglycolate, and 3 – 35 parts of thiourea, said composition having a shelf stability under ambient conditions of at least 3 months.
6. Composition according to claim 5, wherein said composition contains from 10 – 20 parts of calcium thioglycolate and 5 – 15 parts of thiourea.
7. Composition according to claim 1, wherein said composition consists essentially of water, about 0.1 – 1.0 weight percent of sodium silicate, about 5 – 10 weight percent of calcium thioglycolate, and about 3 – 7 weight percent of thiourea.
8. Composition according to claim 1, wherein said composition is in the form of a cream.

9. Process for removing beard from the face of a Negro male needing such depilation, said process comprising applying a depilating amount of an aqueous composition having a pH of about 11.5 to about 12.7 and comprising, as the essential active ingredients:
 a. one part of at least one alkali metal silicate in an amount of about 0.1 to 1.0 weight percent, based on the total weight of said composition,
 b. 5 to 200 parts of at least one alkaline earth metal acid salt, wherein the acid is selected from the group consisting of thioglycolic acid and thiolactic acid, and
 c. 1 to 50 parts of thiourea to the face of said Negro male and allowing the composition to remain in contact with the face for a period of 4 – 10 minutes, and immediately thereafter removing the composition from contact with the face, said removing step including a water wash.

10. Process according to claim 9, wherein said composition contains one part of sodium metasilicate, from 6 – 50 parts of calcium thioglycolate, and 3 – 35 parts of thiourea.

11. Process according to claim 10, wherein said composition contains from 10 – 20 parts of calcium thioglycolate and 5 – 15 parts of thiourea.

12. Process according to claim 9, wherein said composition consists essentially of water, about 0.1 – 1.0 weight percent of sodium silicate, about 5 – 10 weight percent of calcium thioglycolate, and about 3 – 7 weight percent of thiourea.

13. Process according to claim 9, wherein said aqueous composition is in the form of a cream.

* * * * *